US00PP24519P2

(12) United States Plant Patent
Koppe

(10) Patent No.: US PP24,519 P2
(45) Date of Patent: Jun. 3, 2014

(54) *BEGONIA* PLANT NAMED 'BETULIA CANDY'

(50) Latin Name: *Begonia×hiemalis*
Varietal Denomination: Betulia Candy

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 46 days.

(21) Appl. No.: 13/573,170

(22) Filed: Aug. 27, 2012

(51) Int. Cl.
*A01H 5/00* (2006.01)

(52) U.S. Cl.
USPC ..... Plt./349

(58) Field of Classification Search
USPC ..... Plt./349
See application file for complete search history.

*Primary Examiner* — Annette Para
(74) *Attorney, Agent, or Firm* — C. A. Whealy

(57) ABSTRACT

A new and distinct cultivar of *Begonia* plant named 'Betulia Candy' characterized by its compact, upright, outwardly spreading and mounded plant habit; freely branching habit; dark green-colored leaves; numerous light red purple-colored flowers that are held above and beyond the foliar plane; and excellent postproduction longevity.

2 Drawing Sheets

Botanical designation: *Begonia×hiemalis.*
Cultivar denomination: 'BETULIA CANDY'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'Betulia Candy'.

The new *Begonia* plant is a naturally-occurring whole plant mutation of *Begonia×hiemalis* 'Betulia Bright Pink', disclosed in U.S. Plant Pat. No. 16,842. The new *Begonia* plant was discovered and selected by the Inventor as a single flowering plant from within a population of plants of 'Betulia Bright Pink' in a controlled greenhouse environment in Ermelo, The Netherlands in May, 2008.

Asexual reproduction of the new *Begonia* plant by vegetative cuttings taken in a controlled greenhouse environment in Ermelo, The Netherlands since February, 2009 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Betulia Candy'. These characteristics in combination distinguish 'Betulia Candy' as a new and distinct *Begonia* plant:

1. Compact, upright, outwardly spreading and mounded plant habit.
2. Freely branching habit.
3. Dark green-colored leaves.
4. Numerous light red purple-colored flowers that are held above and beyond the foliar plane.
5. Excellent postproduction longevity.

Plants of the new *Begonia* differ primarily from plants of the parent, 'Betulia Bright Pink', in flower color. Plants of the new *Begonia* have lighter red purple-colored flowers than plants of 'Betulia Bright Pink'.

Plants of the new *Begonia* can be compared to plants of *Begonia×hiemalis* 'Betulia Light', disclosed in U.S. Plant Pat. No. 13,656. In side-by-side comparisons conducted in Ermelo, The Netherlands, plants of the new *Begonia* differed primarily from plants of 'Betulia Light' in flower color as plants of 'Betulia Light' had white-colored flowers with pink-colored centers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Betulia Candy' grown in a container.

The photograph on the second sheet are close up views of the upper and lower surfaces of typical leaves (right) and upper, lateral and lower surfaces of developing and open flowers of 'Betulia Candy' (left).

DETAILED BOTANICAL DESCRIPTION

The aforementioned photographs and following observations and measurements describe plants grown during the spring in 13-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were pinched one time and were 13 weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'Betulia Candy'.

Commercial classification: Elatior *Begonia*.

Parentage: Naturally-occurring whole plant mutation of *Begonia×hiemalis* 'Betulia Bright Pink', disclosed in U.S. Plant Pat. No. 16,842.

Propagation:

*Type.*—By terminal vegetative cuttings.

*Time to develop roots.*—About 20 days at temperatures of 20° C. Time to produce a rooted young plant: About five weeks at temperatures of 20° C.

*Root description.*—Fine, fibrous; white to orange brown in color.

*Rooting habit.*—Freely branching; medium density; plants of the new *Begonia* have not been observed to form tubers.

Plant description:

*Plant habit and form.*—Compact, upright, outwardly spreading and mounded plant habit; overall plant shape roughly globular; flowers held above and beyond the foliar plane.

*Growth habit.*—Moderately vigorous growth habit and moderate growth rate; suitable for 12-cm and larger containers; under optimal environmental and cultural conditions, usually about 13 weeks are required to produce proportional 13-cm potted plants from cuttings; vegetative shoots are formed at basal nodes and flowering shoots are formed at upper nodes.

*Branching habit.*—Freely branching habit; when pinched, about eleven lateral branches develop.

*Plant height.*—About 23.5 cm.

*Plant width.*—About 36.1 cm.

*Lateral branches.*—Length: About 11.5 cm. Diameter: About 8 mm. Internode length: About 1.9 cm. Angle: About 45° from vertical. Texture: Smooth, sparsely pubescent. Color, developing: Close to N199C. Color, fully developed: Close to 152B strongly tinged with close to 181B.

*Leaves.*—Arrangement: Alternate; simple. Length: About 8.8 cm. Width: About 8.2 cm. Shape: Broadly ovate to roughly deltoid. Apex: Acute. Base: Cordate to oblique. Margin: Bi-serrate; laciniate. Texture, upper and lower surfaces: Smooth, glabrous; velvety. Venation pattern: Palmate. Color: Developing leaves, upper surface: Close to N137C. Developing leaves, lower surface: Close to 148A. Fully expanded leaves, upper surface: Darker than between 147A and N189A; venation, close to 138A. Fully expanded leaves, lower surface: Between 148B and 191A; venation, close to 148A. Petioles: Length: About 4.6 cm. Diameter: About 4 mm. Texture, upper and lower surfaces: Sparsely to moderately pubescent. Color, upper and lower surfaces: Close to 179A; at leaf attachment, close to 178A to 178B. Stipules: Length: About 1 cm. Width: About 7 mm. Shape: Broadly ovate. Margin: Entire. Texture, upper and lower surfaces: Smooth, glabrous. Color, upper and lower surfaces: Close to 144C; venation, close to 144A.

Flower description:

*Flower form and flowering habit.*—Semi-double rotate flowers arranged in axillary compound cymes; usually about eight flowers per cyme, numerous cymes in flower simultaneously and about 450 flowers developing per plant; flowers face upright to outwardly and are positioned above and beyond the foliar plane. Natural flowering season: Plants begin flowering about six weeks after pinching; plants flower continuously year round regardless of nyctoperiod, however plants are more freely flowering from autumn to spring.

*Flower longevity.*—Individual flowers last about ten days on the plant; flowers not persistent; flowering plants have excellent postproduction longevity and typical maintain good substance for about seven weeks under interior conditions.

*Fragrance.*—None detected.

*Inflorescence height.*—About 11.9 cm.

*Inflorescence diameter.*—About 10.6 cm.

*Flower buds.*—Length: About 1.6 cm. Diameter: Ranging from about 5 mm to 17 mm. Shape: Reniform, flattened. Color: Close to 51B; towards the base, close to 51C.

*Flowers.*—Shape: Rotate; semi-double. Diameter: About 5.3 cm. Depth (height): About 2.5 cm.

*Tepals.*—Quantity per flower: About four arranged in a single whorl. Length: About 3.6 cm. Width: About 3 cm. Shape: Broadly oblong to broadly ovate or broadly obovate. Apex: Rounded. Margin: Entire. Texture, upper and lower surfaces: Smooth, glabrous; slightly velvety. Color: When opening, upper surface: Close to N57D. When opening, lower surface: Close to 54C. Fully opened, upper surface: Close to N57D; with development, color becoming closer to 49B tinged with close to 62B. Fully opened, lower surface: Close to 62A to 62C; with development, color becoming closer to 49A to 49B and towards the base, tinged with close to 150D.

*Tepaloids.*—Quantity per flower: About eight arranged in about two whorls. Length: About 1.7 cm. Width: About 1.6 cm. Shape: Obovate to broadly elliptic. Apex: Rounded. Margin: Entire. Texture, upper and lower surfaces: Smooth, glabrous; slightly velvety. Color: When opening, upper surface: Close to N57D. When opening, lower surface: Close to 54C. Fully opened, upper surface: Close to N57D; with development, color becoming closer to 49B tinged with close to 62B. Fully opened, lower surface: Close to 62A to 62C; with development, color becoming closer to 49A to 49B and towards the base, tinged with close to 150D.

*Peduncles.*—Length: About 4.8 cm. Diameter: About 3 mm. Angle: About 45° from lateral branch axis. Texture: Smooth, glabrous. Color: Close to 146C.

*Pedicels.*—Length: About 2.8 cm. Diameter: About 2 mm. Angle: About 40° from peduncle axis. Texture: Smooth, glabrous. Color: Close to 144A to 144B.

*Reproductive organs.*—Stamens: None observed. Pistils: None observed.

*Seeds and fruits.*—Seed and fruit development have not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'Betulia Candy' as illustrated and described.

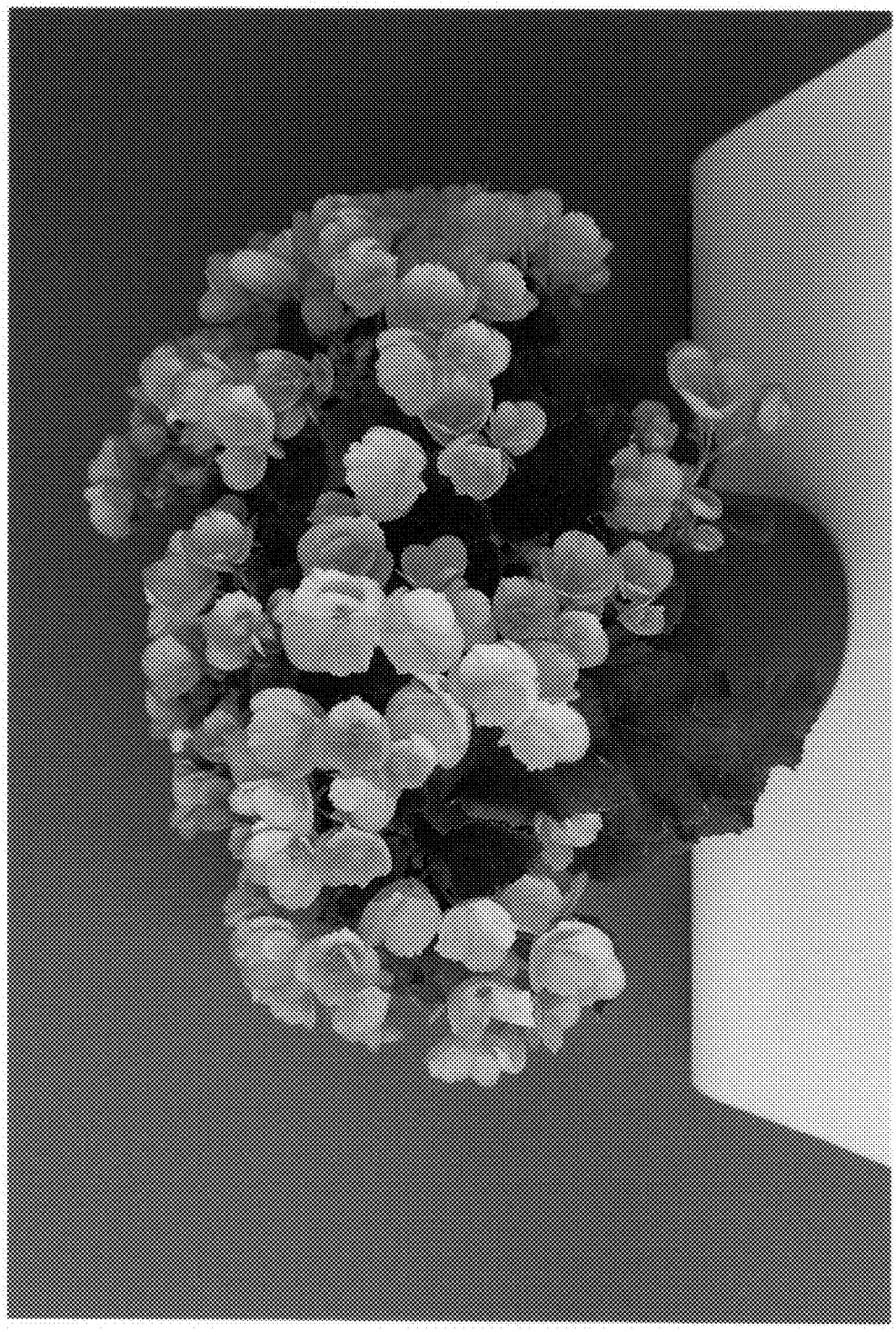

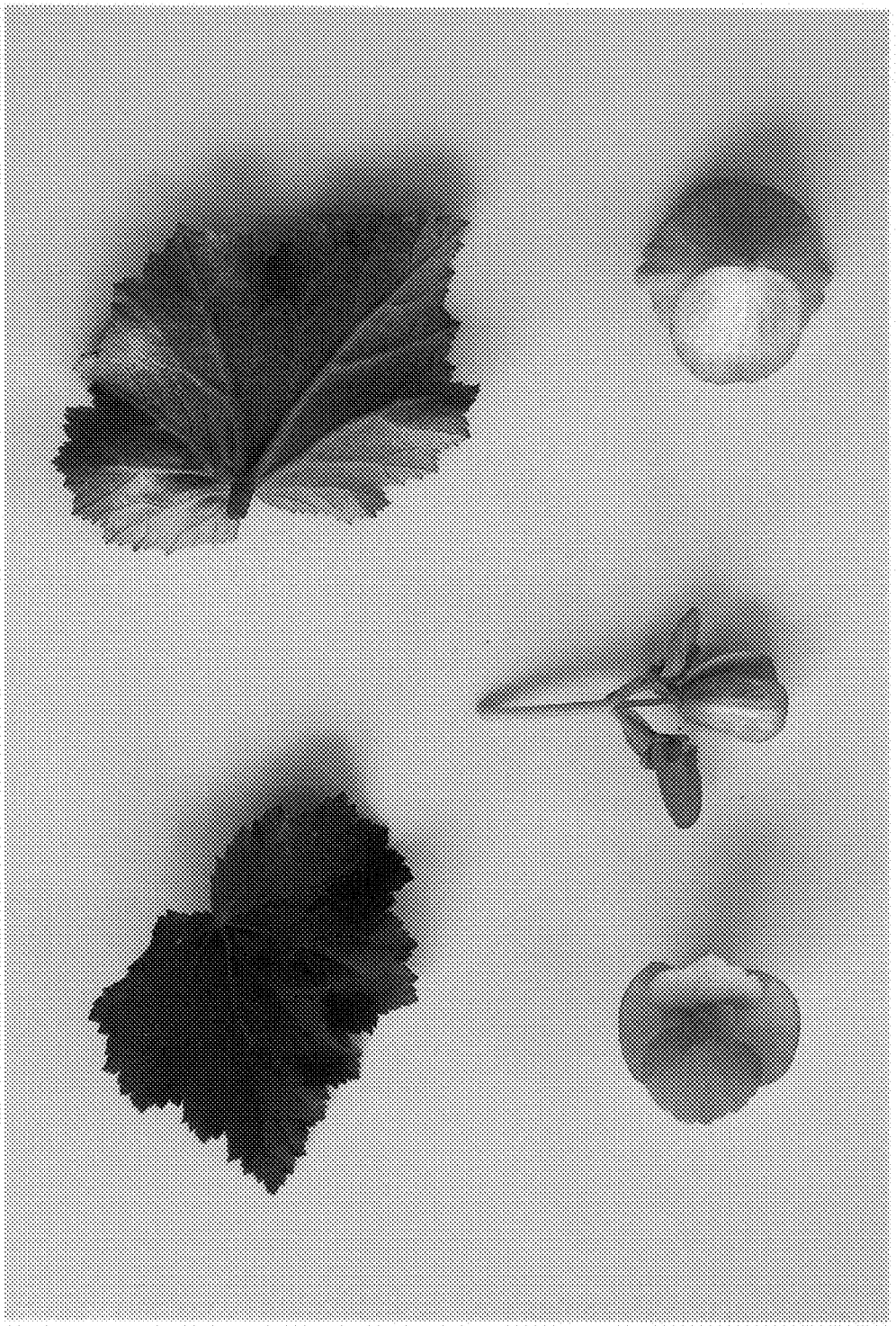

* * * * *